US012661261B2

(12) United States Patent
Yan et al.

(10) Patent No.: US 12,661,261 B2
(45) Date of Patent: Jun. 23, 2026

(54) PHACOEMULSIFICATION HANDLE WITH SENSOR AND SURGE CONTROL SYSTEM AND METHOD

(71) Applicant: INNOLCON MEDICAL TECHNOLOGY (SUZHOU) CO., LTD., Jiangsu (CN)

(72) Inventors: Zhongyu Yan, Irvine, CA (US); Chunjie Cheng, Jiangsu (CN); Fuyuan Wang, Jiangsu (CN); Zhenzhong Liu, Jiangsu (CN); Hui Wang, Jiangsu (CN); Wei Luo, Jiangsu (CN)

(73) Assignee: INNOLCON MEDICAL TECHNOLOGY (SUZHOU) CO., LTD., Jiangsu (CN)

( * ) Notice: Subject to any disclaimer, the term of this patent is extended or adjusted under 35 U.S.C. 154(b) by 868 days.

(21) Appl. No.: 17/628,475

(22) PCT Filed: Apr. 13, 2020

(86) PCT No.: PCT/CN2020/084411
§ 371 (c)(1),
(2) Date: Jun. 14, 2022

(87) PCT Pub. No.: WO2021/012720
PCT Pub. Date: Jan. 28, 2021

(65) Prior Publication Data
US 2023/0190525 A1      Jun. 22, 2023

(30) Foreign Application Priority Data

Jul. 23, 2019    (CN) .......................... 201910666176.3

(51) Int. Cl.
*A61F 9/007*      (2006.01)
*A61M 1/00*      (2006.01)

(52) U.S. Cl.
CPC ......... *A61F 9/00745* (2013.01); *A61M 1/774* (2021.05); *A61M 2210/0612* (2013.01)

(58) Field of Classification Search
CPC ............... A61F 9/00745; A61M 1/774; A61M 2210/0612; A61B 17/32; A61B 2017/32
See application file for complete search history.

(56) References Cited

U.S. PATENT DOCUMENTS 5,478,338 A * 12/1995 Reynard ................. A61F 9/008
                                                    606/17
8,202,243 B2     6/2012 Morgan
                        (Continued)

FOREIGN PATENT DOCUMENTS

CN          1954788 A      5/2007
CN        104161618 A      11/2014
                    (Continued)

*Primary Examiner* — Katherine H Schwiker
*Assistant Examiner* — Zehra Jaffri
(74) *Attorney, Agent, or Firm* — Seed Intellectual Property Law Group LLP

(57)          ABSTRACT
An ultrasonic phacoemulsification handpiece with a sensor and a surge control system and a method. The central aspiration lumen of the ultrasonic phacoemulsification handpiece consists of two components of plug-in loose fit: a fixed lumen and an extension lumen; a small pressure sensor is mounted on the extension lumen, but still able to keep the easy-to-use size and maintain the ultrasonic performance of the handpiece. The extension lumen minimizes the effect of ultrasonic vibration on the sensor while maintaining sufficient stiffness for installing and removing the phacoemulsification tip. The design of the handpiece transducer reduces the effect of this sensor installation on the ultrasonic performance. For ultrasonic phacoemulsification cataract removal surgery, the short distance from the pressure sensor to the surgical site provides a technical solution for reliably controlling the risk of the post occlusion surge.

20 Claims, 3 Drawing Sheets

(56) References Cited

U.S. PATENT DOCUMENTS

| 10,182,940 B2 | 1/2019 | Chandrakant et al. |
| 10,314,953 B2 | 6/2019 | Ovchinnikov et al. |
| 2005/0209621 A1* | 9/2005 | Gordon ............... A61M 3/0258 |
| | | 606/167 |
| 2007/0255196 A1* | 11/2007 | Wuchinich .......... A61F 9/00745 |
| | | 604/22 |
| 2007/0255304 A1* | 11/2007 | Roschak .......... A61B 17/32053 |
| | | 623/23.72 |
| 2008/0319374 A1 | 12/2008 | Zacharias |
| 2015/0157501 A1* | 6/2015 | Bourne ................... A61M 1/85 |
| | | 604/22 |
| 2016/0213515 A1 | 7/2016 | Chon et al. |
| 2016/0346123 A1* | 12/2016 | Koplin ................ A61M 3/0202 |
| 2018/0049920 A1 | 2/2018 | Charles |
| 2018/0056328 A1* | 3/2018 | Downey .............. B06B 1/0246 |
| 2018/0085131 A1 | 3/2018 | Merza et al. |
| 2018/0193193 A1* | 7/2018 | Kahook .............. A61F 9/00772 |

FOREIGN PATENT DOCUMENTS

| CN | 105007974 A | 10/2015 |
| CN | 208464423 U | 2/2019 |
| CN | 110338970 A | 10/2019 |
| WO | WO-9003150 A1 * | 4/1990 |
| WO | 00/53136 A1 | 9/2000 |
| WO | 2017/131930 A2 | 8/2017 |

* cited by examiner

PHACOEMULSIFICATION HANDLE WITH SENSOR AND SURGE CONTROL SYSTEM AND METHOD

BACKGROUND

Technical Field

The present invention relates to medical device field, in particular to an ultrasonic phacoemulsification cataract removal surgery (using ultrasonic driven needle to break, emulsify and aspirate cataractous lens) using ultrasonic handpiece and surge control system and method.

Description of the Related Art

The ultrasonic phacoemulsification cataract removal surgical system usually consists of three main components: console, ultrasonic phacoemulsification handpiece, irrigation/aspiration fluidic system. A simple ultrasonic phacoemulsification system is shown in FIG. 1, which includes console 101, ultrasonic phacoemulsification handpiece 105, irrigation/aspiration fluid system. The console 101 provides drive energy as well as a user interface to receive and process signals from different subsystems. The irrigation/aspiration fluidic system is usually comprised of motor 102, fluidic cassette 103, and fluid tubing 104, which is generally equipped with a pressure/vacuum sensor to measure and control the negative pressure in the aspiration line. In current conventional designs, the pressure/vacuum sensor is mounted in the fluidic cassette 103. The ultrasonic phacoemulsification handpiece 105 is connected to the fluidic cassette 103 by a fluidic tubing 104, which is generally about two meters long. The ultrasonic phacoemulsification handpiece 105 is connected to the console 101 by the handpiece cable 106; the handpiece cable 106 usually contains an ultrasonic signal line.

In ultrasonic phacoemulsification cataract removal surgery, maintaining a suitable intraocular pressure (IOP) and the stability of the eye chamber play a big role in safety. In normal fluid flow, the aspiration volume of the fluid and the irrigation entering the eye anterior chamber are balanced, so that the eye chamber is stable near the preset eye pressure IOP value. But if the phacoemulsification tip is occluded by tissue fragments, this is a frequent occurrence, negative pressure will be built up in the aspiration line. When due to strong aspiration pressure or ultrasonic vibration of the phacoemulsification tip, etc., the occluded tissue fragments are broken away or removed, the liquid in the chamber will be swiftly sucked away by the built-up negative pressure. If the aspirated liquid volume is greater than the inflow volume, the intraocular pressure will decrease, the eye chamber will flatten or even collapse, the whole process occurs in a very short time. This phenomenon is called post occlusion surge (POS) in ultrasonic phacoemulsification cataract surgery, and the fluctuation of eye chamber caused by the surge makes operation more difficult and even causes surgical complications.

The severity of the surge is mainly affected by the following aspects: the inner diameter of the phacoemulsification tip, the IOP setting of the eye pressure, the negative pressure when the occlusion is broken, the size and hardness of the aspiration tubing, etc. In general, small internal diameter of the phacoemulsification tip, high IOP setting, low maximum vacuum setting, small and hard aspiration tubing can help to reduce surge, but these techniques have certain limitations and each has their own disadvantage.

Therefore, if the scenario of suddenly clearance of the occlusion in the aspiration line can be detected in time, and the built-up negative pressure is released in time, then the post occlusion surge will be reduced or even avoided. For the ultrasonic phacoemulsification system currently available on market, as mentioned above, the pressure/vacuum sensor is placed in the fluidic cassette, which is mounted on the console and connected to the ultrasonic phacoemulsification handpiece via an irrigation/aspiration fluidic tubing approximately 2 meter long. Because aspiration occlusion usually occurs in the chamber of the eye, such a long tubing causes the detection of occlusion clearance to be delayed, so that the delayed signal cannot be used to effectively reduce the surge.

On the other hand, the ultrasonic phacoemulsification handpiece is very close to the eye surgery spot. If the ultrasonic phacoemulsification handpiece on the aspiration lumen is placed with a small pressure sensor, the occlusion clearance can be detected in a timely manner. However, with the existing ultrasonic phacoemulsification handpiece, ultrasonic vibration can affect or even damage the placed pressure sensor, which in turn reduces the ultrasonic performance of the handpiece. Patent documents US20180049920A1, U.S. Pat. No. 10,182,940B2 published the placement of sensor in the ultrasonic phacoemulsification handpiece, but did not give a technical solution how to place the sensor, how to prevent the impact of ultrasonic vibration on the sensor, and how to reduce the impact of sensor placement on the ultrasonic performance.

Therefore, it is necessary to propose a new ultrasonic phacoemulsification handpiece design to be suitable for sensor installation, thus reduce the performance impact on each other, in the meanwhile using this ultrasonic phacoemulsification handpiece with sensor to achieve a reduction or even avoid the risk of post occlusion surge.

BRIEF SUMMARY

In view of this, provided is an ultrasonic phacoemulsification handpiece for cataract removal surgery (using ultrasonic driven needle to break, emulsify, and aspirate cataractous lens) and corresponding surge control system and method.

In order to solve the above technical problems, the technical scheme is:

An ultrasonic phacoemulsification handpiece integrated with a sensor, comprising a handpiece housing, a phacoemulsification tip arranged at the distal end of the handpiece housing, an aspiration connector at the proximal end of the handpiece housing, and a transducer part and an extension part are arranged inside the handpiece housing. The transducer part comprises a horn and a driving element; the distal threaded connection of the horn is connected to the phacoemulsification tip, and the proximal end of the horn is provided with a fixed lumen. The extension part comprises an extension lumen and a sensor mounted on the extension lumen. The extension lumen and the fixed lumen are plugged loose fit and the relative rotation from each other is prevented; the inner bore of the two connected parts is connected with the phacoemulsification tip to form an aspiration channel.

Preferably, the sensor is a piezoelectric resistance microelectromechanical (Piezoresistive MEMS) pressure sensor.

Preferably, the sensor is mounted to the side of the extension lumen by means of adhesive bonding, and the wires of the sensor are arranged in the ultrasonic phacoemulsification handpiece cable.

Preferably, the extension part comprises a sealed adhesive elastomer, which is covered on the outside of the connection area between the extension lumen and the fixed lumen.

Preferably, the extension lumen and the fixed lumen have an anti-rotation structure at their connecting ends.

Preferably, the driving element is arranged around the periphery of the horn, fixed by an end mass.

Preferably, the protruded length of the distal end of the fixed lumen from the distal end of the end mass shall not exceed one eighth of the wavelength of the working frequency of the handpiece.

Preferably, the transducer part comprises the amplifying section and the driving section, and the diameter of the amplifying section is less than one-half of the diameter of the driving section.

Preferably, the length of the driving section is between one quarter and one half of the wavelength of the horn at the operating frequency of the handpiece.

Preferably, the driving element is piezoelectric ceramic.

Preferably, the horn and the fixed lumen are manufactured as one body, or rigidly fixed together.

Preferably, the handpiece housing is equipped with irrigation tube, the proximal end of the irrigation tube is the irrigation connector, which is used to connect to the irrigation source.

Provided is an ultrasonic phacoemulsification handpiece integrated with a sensor, comprising a handpiece housing, a phacoemulsification tip arranged at the distal end of the handpiece housing, an aspiration connector at the proximal end of the handpiece housing, and a transducer part and an extension part are arranged inside the handpiece housing; the inner bore of the transducer part and the extension part connected with the aspiration connector to form an aspiration channel; the extension part is mounted with a sensor; the transducer part and the extension part are plugged loose fit and the relative rotation between the two is prevented.

Preferably, the transducer part comprises a horn and driving element, the driving element is piezoelectric ceramic, and the distal threaded connection of the horn is connected with phacoemulsification tip. The extension part comprises an extension lumen and on side of it a sensor is mounted by adhesive bonding. The distal end of the extension lumen and the proximal end of the horn are plug-in loose fit and the relative rotation between the two is prevented. The inner bore of the connected extension lumen and the horn are connected with the phacoemulsification tip to form an aspiration channel.

Provided is a surge control system, comprising:

an ultrasonic phacoemulsification handpiece with a sensor as described above, connected to the console by the handpiece cable, and the console has built-in ultrasonic generator;

an irrigation source connected to the ultrasonic phacoemulsification handpiece by an irrigation tubing;

a vacuum generating device connected to the ultrasonic phacoemulsification handpiece by an aspiration tubing, the other side of which is connected to a waste fluidic bag by a waste fluidic cavity and a waste fluidic channel;

a normally closed aspiration valve, arranged between the aspiration line and the waste fluidic cavity, connected to the console by the first signal line; between the aspiration valve and the waste fluidic cavity is a negative pressure release channel;

Preferably, the irrigation line is equipped with an irrigation sensor and an irrigation valve and they are connected to the console by the second and third signal lines.

Provided is a surge control method, comprising the following steps:

S1. provide an ultrasonic phacoemulsification handpiece with a sensor, it comprises handpiece housing, phacoemulsification tip arranged at the distal end of the handpiece housing, aspiration connector at the proximal end of the handpiece housing; inside the handpiece housing are transducer part and extension part, the inner bore of the transducer part and the extension part are connected with the aspiration connector to form an aspiration channel; the extension part is equipped with a sensor; the transducer part and the extension part are plug-in loose fit and the relative rotation from each other are prevented. The ultrasonic phacoemulsification handpiece is connected to the console by a handpiece cable, and the console has a built-in ultrasonic generator;

S2. provide an irrigation source, through the irrigation tubing connected to the ultrasonic phacoemulsification handpiece;

S3. provide a vacuum generating device, through the aspiration tubing connected to the ultrasonic phacoemulsification handpiece, the other side connected to the waste fluidic bag through the waste fluidic cavity and waste fluidic channel;

S4. provide a normally closed aspiration valve, arranged between the aspiration line and the waste fluidic cavity, connected to the console by the first signal line; between the aspiration valve and the waste fluidic cavity is a negative pressure release channel;

S5. the sensor measures the pressure value in the aspiration channel, the console calculates the changing rate of the pressure; according to the fluidic system parameters in the console set a threshold, once the changing rate of the pressure is greater than the threshold, the console opens the aspiration valve, the negative pressure in the aspiration channel is released quickly through the negative pressure release channel.

Preferably, the fluidic system parameters include but are not limited to intraocular pressure IOP, equivalent irrigation bottle height, phacoemulsification tip size, and the maximum vacuum setting.

The beneficial effects of the present invention are mainly reflected in:

1. The central lumen of the ultrasonic phacoemulsification handpiece comprises two sections by loose fit: fixed lumen and extension lumen; a small pressure sensor is attached on the extension lumen, but the easy-to-use size and the ultrasonic performance of the handpiece are still able to be maintained.

2. The extension lumen design and installation scheme (ultrasonic vibration decoupled by loose fit) minimize the impact of ultrasonic vibration on the sensor, while maintaining sufficient stiffness to install and remove the phacoemulsification tip.

3. The handpiece transducer design reduces the impact of the sensor installation on the ultrasonic performance.

4. For ultrasonic phacoemulsification cataract removal surgery, this closeness of the pressure sensor to the surgical site provides a reliable technical solution to control the risk of surge.

DETAILED DESCRIPTION

Figure 1:
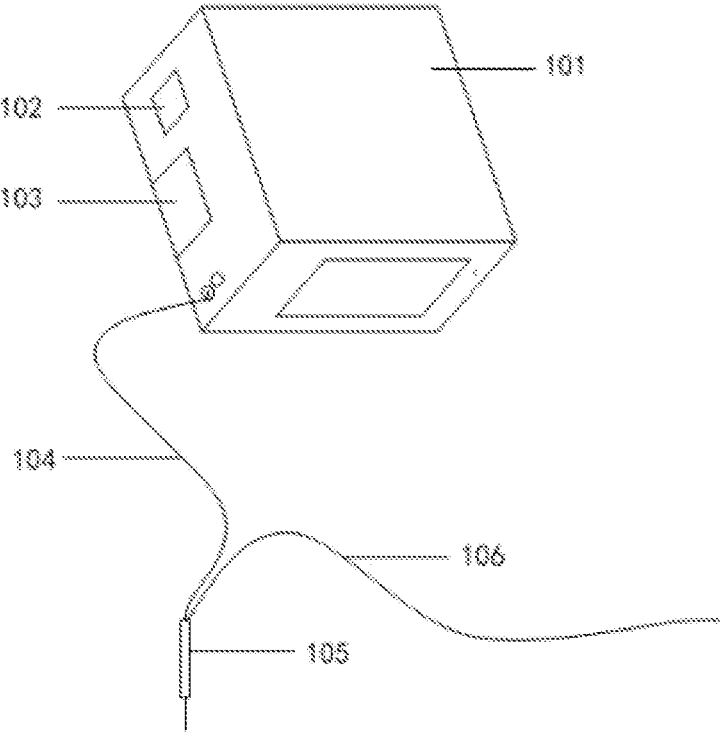
FIG. 1 is a diagram of a simple ultrasonic phacoemulsification system with existing technology.

The following will combine with the specific embodiment shown in the drawings to describe the present invention in detail. However, these embodiments are not limitations to the present invention; the ordinary technical personnel in the art according to these embodiments making the structure, method, or functional transformation are contained in the scope of protection of the present invention.

In the description of the scheme, it should be noted that the terms "center", "up", "down", "left", "right", "front", "back", "vertical", "horizontal", "inside", "outside" and other indications of the orientation or position relationship based on the drawings, only to facilitate the description and simplification of the description, rather than to indicate or imply that the device or component must have a specific orientation, with a specific orientation structure and opera- tion, and therefore cannot be understood as a limitation of the present invention. In addition, the terms "first," "sec- ond," and "third" are used only for descriptive purposes and are not understood to indicate or imply relative importance. Also, in the description of the scheme, the operator is used as the reference, the direction close to the operator is the proximal end, and the direction away from the operator is the distal end.

Figure 2:
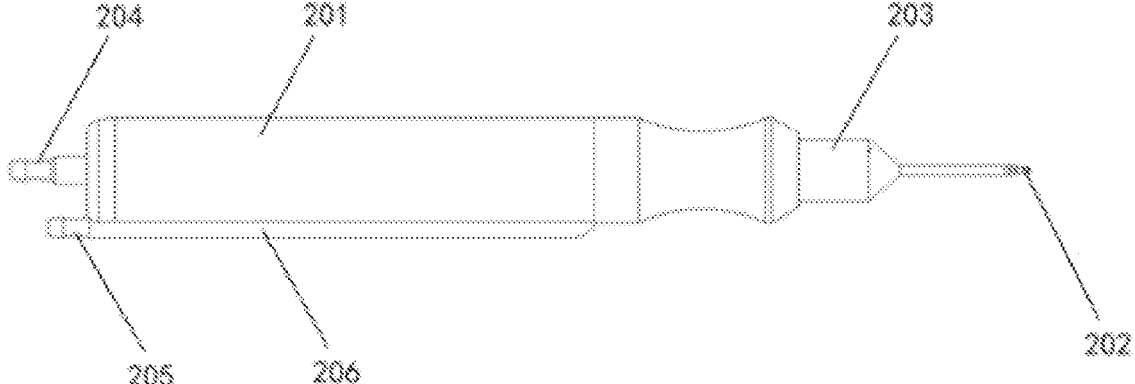
FIG. 2 is a structural diagram of the ultrasonic pha- coemulsification handpiece provided by the preferred embodiment of the present invention.
Figure 3:
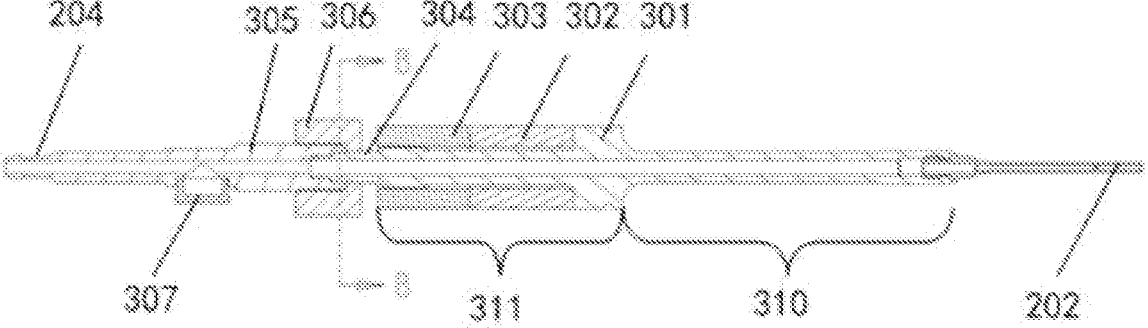
FIG. 3 is a cross-section view of the ultrasonic pha- coemulsification handpiece in FIG. 2, but the housing and the irrigation sleeve are removed.
Figure 5:
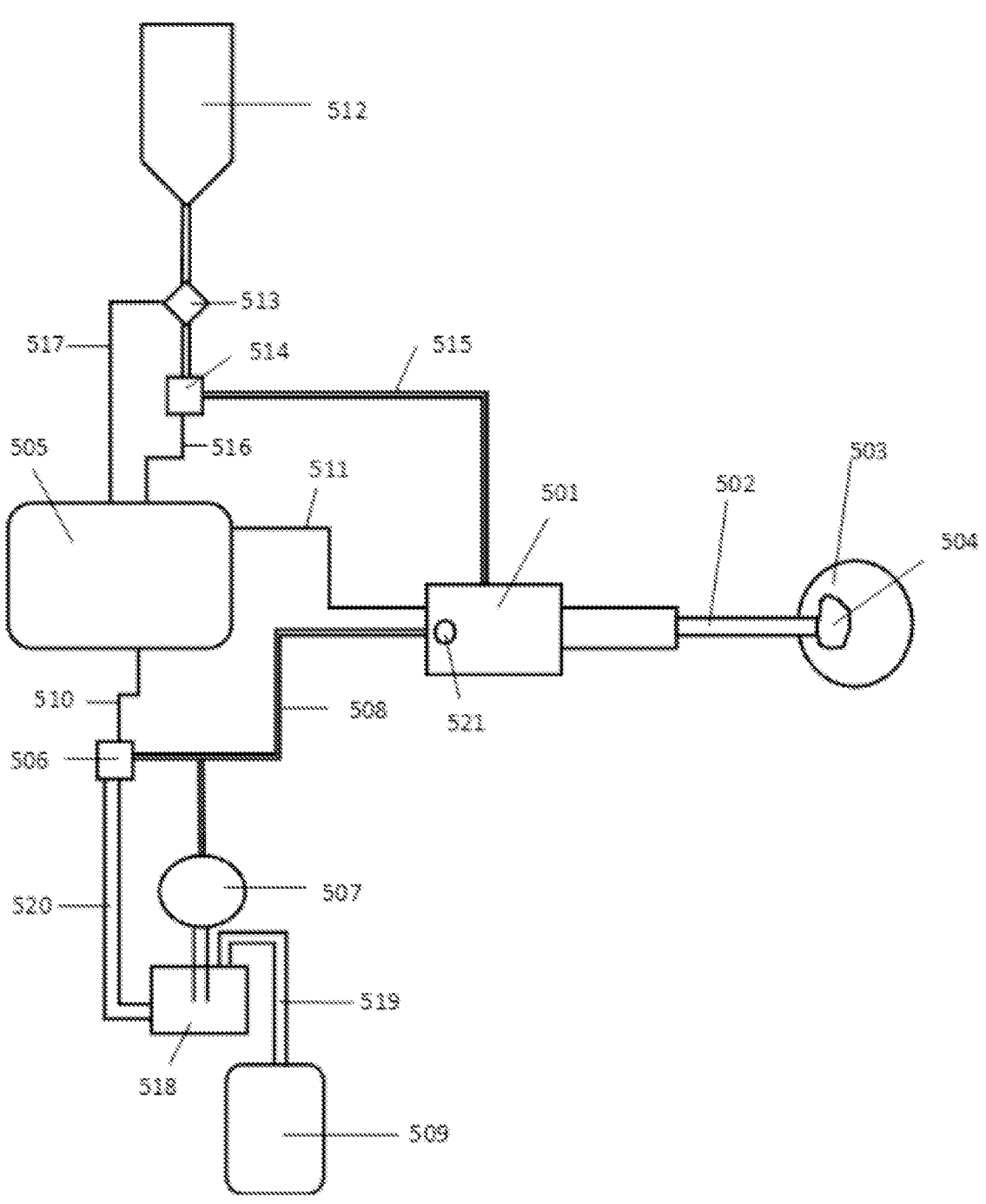
FIG. 5 is the topology diagram of the surge control system provided by the preferred embodiment of the present inven- tion.

As shown in FIGS. 2 and 3, provided is an ultrasonic phacoemulsification handpiece integrated with a sensor; similar to the existing technology, comprising handpiece housing 201, phacoemulsification tip 202 arranged at the distal end of the handpiece housing 201, and aspiration connector 204 at the proximal end of the handpiece housing 201; the aspiration connector is used to connect the vacuum generating device 507 (FIG. 5).

The handpiece housing 201 is also equipped with irriga- tion tube 206, the proximal end of the irrigation tube 206 is irrigation connector 205, and the irrigation connector is used to connect the irrigation source 512 (FIG. 5). At the con- nection area between the phacoemulsification tip 202 and the handpiece housing 201 is provided with an irrigation sleeve 203.

The ultrasonic phacoemulsification handpiece has func- tions of aspiration and irrigation which will not repeated here.

Inside the handpiece housing 201 are a transducer part and an extension part, the transducer part can be more detailed into two sections: amplifying section 310 and driving section 311. The transducer part comprises a horn 301 and drive element 302; the distal end threaded connec- tion of the horn 301 is connected to the phacoemulsification tip 202. The detailed transforming structure of the horn 301 is not the focus of the present invention, so not to be repeated here. In this preferred embodiment, the driving element 302 is arranged on the periphery of the horn 301, fixed by an end mass 303. The driving element 302 is piezoelectric ceramic. The outer diameters of the end mass 303, of the driving element 302 and the maximum diameter of the horn 301 are approximately the same, which form the driving section 311; the small outer diameter segment of the horn 301 forms the amplifying section 310.

The proximal end of the horn 301 is fixed lumen 304, the horn 301 and fixed lumen 304 are manufactured as one body, or both can be made into separate components but rigidly fixed when installed.

The extension part comprises an extension lumen 305, a sensor 307 and a sealing elastomer 306. Specifically, the sensor 307 is mounted by adhesive bonding on side of the extension lumen 305, and the power and signal wires of the sensor 307 are arranged in the ultrasonic phacoemulsifica- tion handpiece cable. The sensor 307 is a piezoresistive MEMS pressure sensor.

In the existing design, the central lumen is one body or rigidly fixed together two components, so there will be strong ultrasonic vibration on the aspiration lumen. If the sensor is fixed to such a lumen, it is easily interfered or even damaged by the ultrasonic vibration. To avoid this, provided between the extension lumen 305 and the fixed lumen 304 is a plug-in loose fit and between the two the relative rotation is prevented, and the connection of the inner bore of the two parts and the phacoemulsification tip 202 forms an aspira- tion channel. The specific plug-in fit can be shown as in FIG. 3, the extension lumen 305 covers over the outer periphery of the fixed lumen 304; it can also be the fixed lumen 304 covers over the outer periphery of the extension lumen 305.

The sealing elastomer 306 is covered on the outside of the connecting area between the extension lumen 305 and the fixed lumen 304. The hardness of the sealing elastomer 306 after cured is between 60-90 Shore A. It should be noted that the loose fit described herein refers to the ultrasonic vibra- tion decoupling of the loose fit; the extension lumen 305 and the fixed lumen 304 do not form a rigid body, so the transmission of ultrasonic vibration to the extension lumen is stopped here. The cured elastomer only acts as a mechani- cal (static or ultra-low frequency transfer) bonding to pre- vent from pulling disengagement, i.e., from longitudinal relative movement; it may also play a role in preventing from rotation, but may not be able to resist the torque of frequent installing and removing of the phacoemulsification tip, so the invention adds the following anti-rotation struc- ture.

Figure 4:
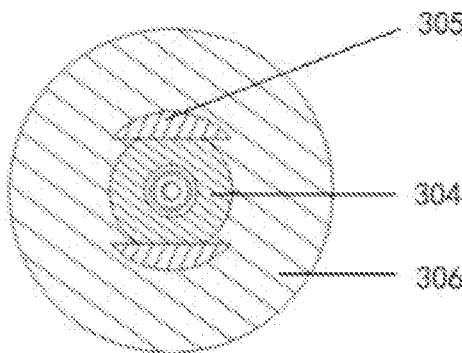
FIG. 4 is a cross-section view in the direction of B-B in FIG. 3.

In practical application, the phacoemulsification tip 202 needs to be installed on the horn or removed frequently, usually connected by thread. When operating, hold the handpiece housing 201 in one hand, hold the wrench on the phacoemulsification tip 202 in other hand, and the torque will be transmitted through the handpiece housing 201 to the connected extension lumen 305, and then to the fixed lumen 304, the distal end of the horn 301. Therefore, an anti- rotation structure needs to be provided on the connecting ends between the extension lumen 305 and the fixed lumen 304. FIG. 4 shows an embodiment of an anti-rotation mating structure in which the ends connected by the two lumens have flat cut surfaces corresponding to each other. Through this design, the extension lumen 305 and the sensor 307 are effectively isolated from the ultrasonic vibration, but still maintain the rigidity of the overall structure for various mechanical operations. Of course, a skill person in the art should be aware that other shapes of anti-rotation mating structure are also allowed.

The above-mentioned addition of the sealing elastomer 306 and the loose fit structure between the extension lumen 305 and fixed lumen 304 have been able to effectively reduce the effect on the ultrasonic performance of transducer. However, in order to further minimize this performance degradation and maintain the ultrasonic performance of the handpiece, the invention also provides the following design scheme for the ultrasonic transducer.

The protruding length of the proximal end of the fixed lumen 304, that is, the length from the proximal end of the end mass 303 to the proximal end of the fixed lumen 304, which does not exceed one eighth of the wavelength of the working frequency of the handpiece, so that the ultrasonic vibration in the place where the extension lumen 305 is connected with the fixed lumen 304 will be very small. The reason is: at end of a large diameter vibrator (in this case, the end mass 303) is a small diameter vibrator (in this case, fixed lumen 304 outstretched part), if the small diameter vibrator length is close to ¼ wavelength of the operating frequency, the end of the small diameter vibrator will produce a strong vibration. Therefore, the shorter the protruding length, the smaller the vibration amplification.

The diameter of the amplifying section 310 is less than one-half of the diameter of the driving section 311, in order to maintain the high efficiency of the transducer, reduce the amplitude of the driving section 311. The reason is: for factors causing the ultrasonic amplitude amplification by a horn, one of them is the area ratio of the front end and rear end of the horn; the front end is the amplifying section 310, the rear end is the driving section 311; the smaller the diameter ratio of the two sections, the larger the amplification effect, therefore, only a small amplitude in the driving section, it can produce a large amplitude at the end of the amplifying section.

The length of the driving section 311 is between one-fourth and one-half of the wavelength of the horn at the handpiece operating frequency, in order to maintain the loading capacity and a suitable size of the handpiece. The reason is: if the driving section 311 is too short, shorter than ¼ wavelength of the horn, the handpiece loading capacity will be too weak, i.e., a little obstruction of the phacoemulsification tip can make the overall handpiece vibration become very weak; If the driving section 311 is too long, exceeding ½ wavelength of the horn, not only does the loading capacity does not increase proportionally, but the overall handpiece volume becomes too bulky.

Also provided is a surge control system, as shown in FIG. 5, comprising:

an ultrasonic phacoemulsification handpiece 501 integrated with a sensor 521 (307 in FIG. 3), it is connected to the console 505 via the handpiece cable 511, and the console 505 has a built-in ultrasonic generator; the ultrasonic phacoemulsification handpiece 501 is equipped with a phacoemulsification tip 502 (202 in FIG. 3);

an irrigation source 512, it is connected to the ultrasonic phacoemulsification handpiece 501 by irrigation line 515, and the irrigation line 515 is equipped with irrigation sensor 513 and irrigation valve 514; both of them are connected to the console 505 by the second and third signal lines 516 and 517;

a vacuum generating device 507, it is connected to the ultrasonic phacoemulsification handpiece 501 by aspiration tubing 508, and the other side of the vacuum generating device 507 is connected to the waste fluidic bag 509 by the waste cavity 518 and the waste fluidic channel 519.

Consistent with the existing technology, ultrasonic vibration through the phacoemulsification tip 502 is transmitted to the eye 503. In the aspiration line the aspirating negative pressure is produced by the vacuum generating device 507.

The cataractous tissue 504 is broken and aspirated out, and the cataract fragment and fluidic mixture are sent to the waste bag 509.

The difference of the present invention is: It includes a normally closed aspiration valve 506, arranged between the aspiration tubing 508 and the waste cavity 518, through the first signal line 510 connected to the console 505; between the aspiration valve 506 and the waste cavity 518 is a negative pressure release channel 520. When the aspiration valve 506 is closed, the aspiration channel comprises only the aspiration tubing 508 and its connected handpiece and tip inner bores, so the negative pressure generated by the vacuum generating device only exists in this channel, and only through the tip inner bore to release. When the aspiration valve is opened, it adds another aspiration channel 520, and this channel is connected to the waste cavity 518 and the waste fluidic bag 509 with the ambient pressure; its opening is much larger than the tip inner bore, so it will be very fast to compensate for the negative pressure in the aspiration channel, that is, rapid release of the negative pressure.

Also provided is a surge control method, including the following steps:

S1, provide an ultrasonic phacoemulsification handpiece 501 integrated with a sensor; the ultrasonic phacoemulsification handpiece comprises a handpiece housing 201, a phacoemulsification tip 202 arranged at the distal end of the handpiece housing 201, an aspiration connector 204 arranged at the proximal end of the handpiece housing 201. In the handpiece housing 201 are a transducer part and an extension part; the interior bore of the transducer part and the extension part connect with the aspiration connector 204 to form an aspiration channel; the extension part is equipped with a sensor 307. The transducer part and the extension part are plug-in loose fit and the relative rotation between the two is prevented. The ultrasonic phacoemulsification handpiece 501 is connected to the console 505 by the handpiece cable 511, and the console 505 has a built-in ultrasonic generator;

S2, provide an irrigation source 512, by irrigation tubing 515 connected to the ultrasonic phacoemulsification handpiece 501;

S3, provide a vacuum generating device 507, by aspiration tubing 508 connected to the ultrasonic phacoemulsification handpiece 501; the other side connected to the waste fluidic bag 509 through the waste fluidic cavity 518 and waste fluidic channel 519;

S4, provide a normally closed aspiration valve 506, arranged between the aspiration line 508 and the waste fluidic cavity 518, through the first signal line 510 connected to the console 505; between the aspiration valve 506 and the waste fluidic cavity 518 is the negative pressure release channel 520;

S5, the sensor 521 measures the pressure value in the aspiration channel, the console 505 calculates the rate of pressure change, e.g., mmHg/10 ms. According to the fluidic system parameters set a threshold within the console, the fluidic system parameters include but are not limited to intraocular pressure IOP, equivalent irrigation bottle height, phacoemulsification tip 202 diameter size, and maximum vacuum setting. If the rate of pressure change is greater than the threshold because an occlusion is cleared, the console 505 controls the aspiration valve 506 to open, and the negative pressure in the aspiration channel is released quickly through the negative pressure release channel 520, so the surge is avoided.

The above is only the preferred embodiment of the present invention, it should be pointed out that the above preferred embodiment shall not be regarded as a limitation on the present invention, the scope of protection of the present invention shall be defined by the scope of the claims. For ordinary technical personnel in the technical field, in the essence and scope of the present invention, may also make a number of improvements and modifications, these improvements and modifications should also be regarded as the scope of protection of the present invention.

The invention claimed is:

1. A phacoemulsification handpiece, comprising:
a handpiece housing having a distal end and a proximal end;
a phacoemulsification tip arranged at the distal end of the handpiece housing;
an aspiration connector arranged at the proximal end of the handpiece housing; and
a transducer part and an extension part arranged inside the handpiece housing, wherein the transducer part comprises a horn and a driving element being piezoelectric ceramic, wherein a distal end of the horn is threaded to threadedly couple to the phacoemulsification tip, and a proximal end of the horn is a fixed lumen,
wherein the extension part comprises an extension lumen coupled to the fixed lumen in a loose fit connection that ultrasonically decouples the fixed lumen from the extension lumen, the extension part further including a sensor attached to the extension lumen,
wherein at least one of the extension lumen covers over an outer periphery of the fixed lumen, or the fixed lumen covers over an outer periphery of the extension lumen, which prevents a circumferential rotation between the extension lumen and the fixed lumen, and
wherein inner bores of the extension lumen and the fixed lumen are connected with the phacoemulsification tip to form an aspiration channel.

2. The phacoemulsification handpiece according to claim 1 wherein the sensor is a piezoresistive microelectromechanical pressure sensor.

3. The phacoemulsification handpiece according to claim 1 wherein the sensor is attached to a side of the extension lumen by adhesive bonding, and wherein a wire of the sensor is arranged in a phacoemulsification handpiece cable.

4. The phacoemulsification handpiece according to claim 1, wherein the extension part includes a sealing elastomer and is covered by the sealing elastomer on an outside of a connecting area between the extension lumen and the fixed lumen, and wherein the sealing elastomer is a mechanical bond that prevents longitudinal movement of the extension lumen relative to the fixed lumen.

5. The phacoemulsification handpiece according to claim 1 comprising an anti-rotation structure including mating flat surfaces at connection ends of the extension lumen and the fixed lumen.

6. The phacoemulsification handpiece according to claim 1 wherein the driving element is fixed on a periphery of the horn by an end mass.

7. The phacoemulsification handpiece according to claim 6 wherein a protruding length of a proximal end of the fixed lumen is a length from a proximal end of the end mass to the proximal end of the fixed lumen, wherein the protruding length does not exceed ⅛ wavelength of an operating frequency of the handpiece.

8. The phacoemulsification handpiece according to claim 1 wherein the transducer part comprises an amplifying section and a driving section, and wherein a diameter of the amplifying section is less than ½ of a diameter of the driving section.

9. The phacoemulsification handpiece according to claim 8 wherein a length of the driving section is between ¼ and ½ of a wavelength of the horn at an operating frequency of the handpiece.

10. The phacoemulsification handpiece according to claim 1 wherein the horn and the fixed lumen are an integral single body or rigidly fixed together.

11. The phacoemulsification handpiece according to claim 1 wherein the handpiece housing includes an irrigation tube, and wherein a proximal end of the irrigation tube is an irrigation connector configured to connect to an irrigation source.

12. A surge control system, comprising:
a console,
a handpiece cable,
the phacoemulsification handpiece as described in claim 1 coupled to the console through the handpiece cable, and wherein the console has a built-in ultrasonic generator,
an irrigation source connected to the phacoemulsification handpiece through an irrigation tubing,
a vacuum generating device connected to the phacoemulsification handpiece through an aspiration tubing, and connected to a waste fluidic bag through a waste fluidic cavity and a waste fluidic channel, and
a normally closed aspiration valve arranged between the aspiration tubing and the waste fluidic cavity and connected to the console through a first signal line, a negative pressure release channel arranged between the aspiration valve and the waste fluidic cavity.

13. The surge control system according to claim 12 wherein the irrigation tubing has an irrigation sensor and an irrigation valve connected to the console through second and third signal lines.

14. A method for using the phacoemulsification handpiece of claim 1, comprising:
connecting an irrigation source to the phacoemulsification handpiece through an irrigation tubing;
connecting the phacoemulsification handpiece to a console through a handpiece cable, and wherein the console has a built-in ultrasonic generator;
connecting a vacuum generating device to the phacoemulsification handpiece through an aspiration tubing, including connecting the vacuum generating device to a waste fluidic bag through a waste fluidic cavity and a waste fluidic channel;
arranging a normally closed aspiration valve between the aspiration line and the waste fluidic cavity, and connecting the normally closed aspiration valve to the console through a first signal line, wherein a negative pressure release channel is arranged between the aspiration valve and the waste fluidic cavity;
using the sensor, measuring a pressure value in the aspiration channel; and
using the console, calculating a rate of pressure change, and setting a threshold in the console according to one or more fluidic system parameters, wherein when the rate of pressure change is greater than the threshold, the console controls the aspiration valve to open, and a negative pressure in the aspiration channel is released through the negative pressure release channel.

15. The method according to claim 14 wherein the fluidic system parameters include an intraocular pressure, an equivalent bottle height, a diameter of the phacoemulsification tip, and a maximum vacuum setting.

16. A phacoemulsification handpiece comprising:

a handpiece housing;

a phacoemulsification tip arranged at a distal end of the handpiece housing;

an aspiration connector arranged at a proximal end of the handpiece housing;

a transducer part and an extension part arranged inside the handpiece housing, wherein inner bores of the transducer part and the extension part are connected with the aspiration connector to form an aspiration channel; and a sensor coupled to the extension part, wherein between the transducer part and the extension part is a plug-in loose fit connection that ultrasonically decouples the transducer part and the extension part and wherein a connecting end of the transducer part includes a mating surface configured to engage with a corresponding mating surface of the extension part to prevent a circumferential rotation between the transducer part and the extension part.

17. The phacoemulsification handpiece according to claim 16 wherein the transducer part comprises a horn and a driving element, and wherein the driving element is piezoelectric ceramic, wherein a distal end of the horn is threaded to threadedly couple with the phacoemulsification tip, wherein the extension part comprises an extension lumen and the sensor fixed on a side of the extension lumen by adhesive bonding, wherein a distal end of the extension lumen and a proximal end of the horn are in a plug-in loose fit that ultrasonically decouples the distal end of the extension lumen and the proximal end of the horn, wherein inner bores of the extension lumen and the horn are connected with the phacoemulsification tip to form an aspiration channel.

18. A phacoemulsification handpiece, comprising:

a housing including a phacoemulsification tip and an aspiration connector;

a transducer inside the housing including a horn and a drive, wherein a distal end of the horn is removably coupleable to the phacoemulsification tip and a proximal end of the horn terminates in a fixed lumen; and an extension assembly including an extension lumen in fluid communication with the fixed lumen and a sensor coupled to the extension lumen, both the extension lumen and the sensor being enclosed in the housing, wherein a plug-in loose fit connection is provided between the extension lumen and the fixed lumen such that the extension lumen ultrasonically decouples from the fixed lumen to prevent vibration of the sensor, and wherein a connecting end of the extension lumen includes a non-circular surface that mates with a further non-circular surface of the fixed lumen to prevent rotation of the extension lumen relative to the fixed lumen.

19. The phacoemulsification handpiece of claim 18, further comprising:

a sealing elastomer at the interface between the fixed lumen and the extension lumen that prevents pulling disengagement of the extension lumen relative to the fixed lumen.

20. The phacoemulsification handpiece of claim 18, wherein the extension lumen is rigid.

* * * * *